(12) United States Patent
Lehoux et al.

(10) Patent No.: US 7,137,811 B2
(45) Date of Patent: Nov. 21, 2006

(54) CATALYTIC COMBUSTION BURNER SYSTEM AND FLASK FITTED WITH SUCH A SYSTEM

(75) Inventors: Jannick Lehoux, Thuit Signol (FR); Corinne Gomez, Incarville (FR)

(73) Assignee: Produits Berger (FR)

( * ) Notice: Subject to any disclaimer, the term of this patent is extended or adjusted under 35 U.S.C. 154(b) by 211 days.

(21) Appl. No.: 10/863,481

(22) Filed: Jun. 8, 2004

(65) Prior Publication Data

US 2004/0265762 A1 Dec. 30, 2004

(30) Foreign Application Priority Data

Jun. 27, 2003 (FR) .................................. 03 07767

(51) Int. Cl.
*F23Q 11/04* (2006.01)
*F23D 3/24* (2006.01)
*F23D 3/40* (2006.01)

(52) U.S. Cl. ................. 431/268; 431/323; 431/328

(58) Field of Classification Search ............... 431/268, 431/326, 328, 320, 319, 323, 170, 325, 7; 60/723
See application file for complete search history.

(56) References Cited

U.S. PATENT DOCUMENTS

| | | | | |
|---|---|---|---|---|
| 2,504,584 A | * | 4/1950 | Ramos ................. | 431/325 |
| 3,240,256 A | * | 3/1966 | Binkley et al. ........... | 431/241 |
| 4,289,478 A | * | 9/1981 | Nitta ................... | 431/344 |
| 4,569,656 A | * | 2/1986 | Shimizu et al. ........... | 431/325 |
| 4,735,568 A | * | 4/1988 | Izumisawa et al. ........ | 431/325 |
| 4,781,577 A | * | 11/1988 | Stewart ............... | 431/320 |
| 6,162,046 A | * | 12/2000 | Young et al. ............. | 431/11 |
| 6,537,061 B1 | * | 3/2003 | Gomez et al. ............ | 431/268 |

FOREIGN PATENT DOCUMENTS

| | | | |
|---|---|---|---|
| DE | 34 36 310 A1 | * | 4/1986 |
| EP | 0 277 875 | | 8/1988 |
| EP | 1 214 948 | | 6/2002 |
| FR | 2 483 782 | | 12/1981 |
| FR | 2 579 465 A | * | 10/1986 |
| FR | 2 680 118 | | 2/1993 |
| WO | 9963267 | | 12/1999 |

* cited by examiner

*Primary Examiner*—Josiah C. Cocks
(74) *Attorney, Agent, or Firm*—Bachman & LaPointe

(57) ABSTRACT

The system has a catalytic combustion burner which comprises on its upper part a peripheral zone supporting a catalyst and a central zone without a catalyst creating a vaporisation zone. The system further comprises a sleeve made of porous material comprising a cavity substantially axial designed to tightly hold a wick purposed to carry a combustible composition to the burner. The sleeve is placed in line with the lower part of the burner so that the combustible composition can move from the pores of the upper part of the sleeve towards the pores of the lower part of the burner.

14 Claims, 2 Drawing Sheets

CATALYTIC COMBUSTION BURNER SYSTEM AND FLASK FITTED WITH SUCH A SYSTEM

BACKGROUND OF THE INVENTION

This invention relates to a catalytic combustion burner system comprising a catalytic combustion burner and constituting a development in catalytic combustion burners known to date. It also relates to a flask fitted with such a burner system.

Catalytic combustion burners used to date are made in porous material and have, on their upper part, a peripheral zone, for example ring shaped, which bears a catalyst and a central zone without a catalyst creating a vaporisation zone.

By way of example, the burners described in the documents EP 0 277 875 B1 and WO 99/63267 under the applicant's name can be quoted.

This type of burner equipped with a wick is generally placed on the neck of a flask containing the combustible composition, the wick being immersed in the said combustible composition.

The combustible composition carried by the wick penetrates via capillarity into the pores of the porous material of the burner.

A certain amount of this composition thus enters into the peripheral zone bearing the catalyst and is subjected therein to catalytic combustion which keeps this peripheral zone at a high temperature.

Another amount of this combustible composition passes through the central zone without a catalyst and is subjected to diffusion via vaporisation therein.

However, it is noted that this diffusion as far as the peripheral and central zones is not ensured in a constant manner whilst in use and that it depends, through experience, to a large extent on the amount of combustible composition in the flask.

This diffusion can also be modified, if need be, following a possible carbonising of the wick which could have created particles that could block some of the pores of the burner.

By experience it is accepted that diffusion, in order to observe a deodorization and a purification of the ambient air, is satisfactory when the consumption of combustible composition is regular and constant.

Now, if regular and constant values of consumption are actually reached with the current catalytic combustion burners, they are principally reached when the flask is about two-thirds filled with combustible composition.

On the other hand, below and above this two-thirds proportion, there is a large variation in the consumption of combustible composition.

When the flask is completely filled up with combustible composition, the supply of combustible composition to the burner is too great and could result in limiting the operating of the burner even to the point of stopping it.

On the contrary, when the flask is no more than a quarter filled with combustible composition, the wick, which is usually made from cotton, no longer ensures the diffusion, in satisfactory operating conditions, of the combustible composition in the burner. Low consumption is then observed.

In addition, when the burner is kept operating until the combustible composition is all used, the wick is modified via carbonisation. Repeated use in such circumstances can still accelerate the ageing of the burner.

It is therefore noted, in every case, whether the flask is insufficiently filled up or, on the contrary, whether it is completely filled up, that the consumption of combustible composition varies significantly and thus restricts the performance in terms of the quality of perfuming, disinfecting and destroying molecules and that a deterioration of the burner can occur.

SUMMARY OF THE INVENTION

The purpose of this invention is therefore to resolve all of the aforementioned inconveniences during the implementation of the known burners and to propose a catalytic combustion burner system allowing for satisfactory and optimal usage of a flask fitted with such a burner system, irrespective of the volume of combustible composition in the said flask and, consequently, to ensure a substantially regular and optimal operating of the catalytic combustion burner, avoiding any risk of carbonising the wick, regardless of the volume of combustible composition in the flask.

According to the invention, this system furthermore comprises a sleeve made from a second porous material, the said sleeve comprising a substantially axial cavity designed to tightly hold a wick whose purpose is to carry a combustible composition to the burner, the said sleeve being placed in line with the lower part of the burner, so that the combustible composition can move from the pores of the upper part of the sleeve towards the pores of the lower part of the burner.

The presence of this sleeve, which is additional to current burners, allows the controlling of the supply of combustible composition to the burner.

Thus, the fact that the upper part of the wick is tightly held by the sleeve allows a restriction in the supply of combustible composition to the burner via the wick, when the flask is completely filled with combustible composition, along its entire height or along the majority of this height.

Additionally, the capillarity of the sleeve is added to the capillarity of the wick to suck a greater amount of combustible liquid than that which would be sucked by the wick alone, when the amount of combustible liquid held in the flask is low.

In addition, the heat transmitted by the burner to the sleeve participates in the moving or the drawing of the combustible composition through the wick towards the catalytic combustion burner.

Thus, thanks to the porous material constituting the sleeve, the supply of combustible composition to the burner is ensured and controlled, even in the event of a low volume in the flask.

The sleeve is made from a second porous material with a porosity which is preferably inferior to the porosity of the first porous material that constitutes the burner.

It is of course possible to adjust and control the supply of combustible composition to the burner by modifying the porosity of the burner on the one hand and of the sleeve on the other hand.

In all cases, the radial and longitudinal capillarity of the wick is largely superior to that of the sleeve.

Thus, and until the combustible composition is used up, the burner is supplied with combustible composition, via capillarity from the wick as well as from the sleeve.

Another advantage lies in the extended choice of the type of wick that can be used in such a burner system.

With current burners, the choice of wick is defined according to several parameters which are notably the wick material, the number of threads it is made up of as well as its method of braiding.

The controlling of the supply of combustible composition to the burner being ensured by means of the sleeve, the influence of the wick, whether that be in terms of structure, material or shape, is of little importance.

The invention also relates to a catalytic combustion flask, designed to contain a combustible composition and to be fitted with, on its neck, a catalytic combustion burner system according to the invention, this system being designed to hold a wick immersed in the said combustible composition.

Thanks to the catalytic combustion burner system according to the invention, and in particular to the presence of the sleeve placed in line with the catalytic combustion burner of known structure, a necessarily precise positioning of the burner system is ensured in the neck of the flask. Indeed, the sleeve plays the role of a slot and forces the precise and adequate positioning of the burner system in the neck of the flask.

BRIEF DESCRIPTION OF THE DRAWINGS

Other advantages and characteristics of the invention will result from the following description, given by way of non-restrictive examples and made in reference to the appended figures in which.

The elements common to FIGS. 1 to 5 are identified by the same number references.

DETAILED DESCRIPTION OF THE PREFERRED EMBODIMENT(S)

Figure 1:
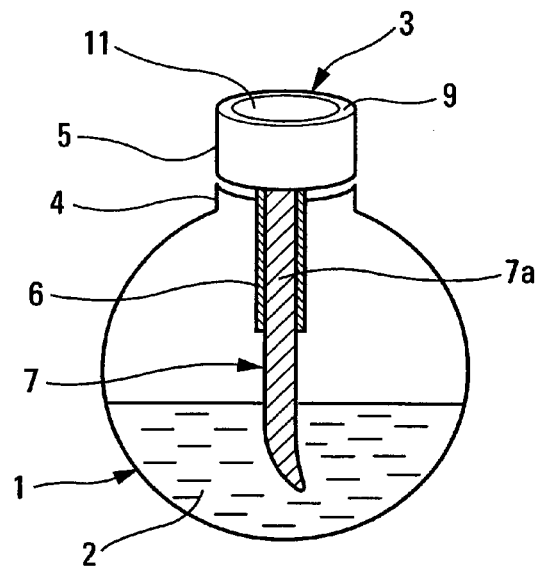
FIG. 1 is a skeletal elevation view of a flask fitted with a catalytic combustion burner system in compliance with this invention.

FIG. 1 represents a catalytic combustion flask 1 designed to contain a combustible composition 2 and to bear, on its upper part, a catalytic combustion burner system 3 in compliance with the invention.

This flask 1 can be of any shape and has a neck 4 capable of being fitted with the catalytic combustion burner system 3.

The catalytic combustion burner system 3 can be fitted, on its lower part, with a support (not represented) allowing it to be inserted, either directly into the neck 4 of the flask 1, or into the central hole of a collar (not represented), the latter being designed to be fitted to the neck 4 of the flask 1.

Supports and collars suitable for the fitting, on the flask 1, of such a burner system 3 were notably described in the application WO 99/63267.

The combustible composition 2 is an appropriate combustible liquid, in compliance with the regulations in force and designed for catalytic combustion and vaporisation.

This combustible composition 2 can notably be an alcohol, in particular isopropyl alcohol, and can further comprise a perfumed material and/or an active material.

This burner system 3 consists of a catalytic combustion burner 5 and a sleeve 6, and is designed to bear a wick 7 immersed in the combustible composition 2.

Figure 2:
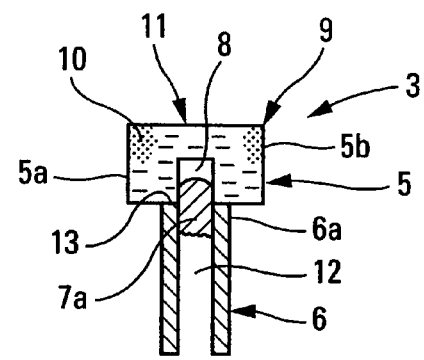
FIG. 2 is a skeletal enlarged axial section view of the burner system represented in FIG. 1, in a first embodiment of this invention, equipped with a wick and designed to be fitted to the flask in FIG. 1.

As represented in detail in FIG. 2, the burner 5 comprises, on its lower part 5*a*, a cavity 8 substantially axial fitted with the wick 7 for the purpose of bringing the combustible composition 2 to the burner 5.

The burner 5 comprises on its upper part 5*b* a peripheral zone 9, of ring shape, which bears a catalyst 10 and a central zone 11 without a catalyst creating a vaporisation zone.

This burner 5 is made from an appropriate first porous material designed to resist the temperatures of at least 400° C. reached in the zone that supports the catalyst during the operating of the burner. This material can notably be a ceramic material, and for example be prepared from kaolin or from cordierite.

The catalyst is for example a metal belonging to Group VIII of the periodic table of elements.

The sleeve 6 of the catalytic combustion burner system 3 according to the invention comprises a cavity 12 substantially axial designed to tightly hold the wick 7 (not represented in FIG. 2) so that the combustible composition 2 can move from the pores of the upper part 6*a* of the sleeve 6 towards the pores of the lower part 5*a* of the burner 5.

The sleeve 6 is placed in line with the lower part 5*a* of the burner 5, so as to align substantially co-axially, on at least part of its surface, the cavity 8 of the burner 5 with the cavity 12 of the sleeve 6.

To ensure the movement of the combustible composition 2 from the pores of the upper part 6*a* of the sleeve 6 towards the lower part 5*a* of the burner 5, the sleeve 6 is made from a second porous material, which can notably be a ceramic material, for example prepared from kaolin or from cordierite.

Preferably, the porosity of the second porous material is less than the porosity of the first porous material constituting the burner 5.

Normally, the first and second porous materials of the burner 5 and the sleeve 6 respectively, are prepared from cordierite.

The lower part 5*a* of the burner 5 and the upper part 6*a* of the sleeve 6 respectively have shapes that complement one another.

In FIG. 2, the parts 5*a* and 6*a* have a flat joining surface 13.

It is however possible to have, instead of a flat joining surface, a type of joining by clamping, as long as the chosen shape of the lower part 5*a* of the burner 5 and the upper part 6*a* of the sleeve 6 allows for the movement of the combustible composition 2 from the sleeve 6 towards the burner 5 to be ensured.

The burner 5 and the sleeve 6 are for example assembled via a porous sealing designed to ensure the movement of the combustible composition from the sleeve 6 towards the burner 5.

In an advantageous embodiment of the burner system 3, which notably avoids the aforementioned sealing operation, the burner 5 and the sleeve 6 constitute one and the same part.

The manufacturing process of the burner system is consequently adapted to allow for the carrying out, if need be, of distinct porous consistencies between the part of the system 3 corresponding to the burner 5 on the one hand and the part of the system 3 corresponding to the sleeve 6 on the other hand.

Figure 3:
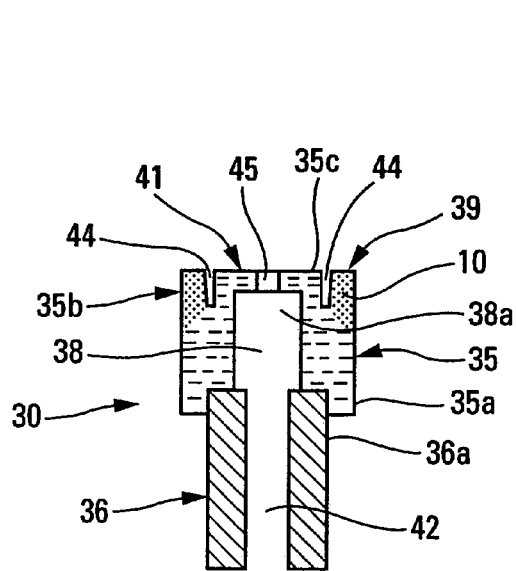
FIG. 3 is a similar view to that of FIG. 2 of a second embodiment of a burner system according to this invention.

Another alternative of the catalytic combustion burner system according to the invention is represented in FIG. 3.

This burner system 30 comprises a catalytic combustion burner 35 and a sleeve 36 joined by clamping, preferably in conjunction with a porous sealing on the lower part 35a of the burner 35 and on the upper part 36a of the sleeve 36.

The cavity 42 of the sleeve 36 is situated in line with the cavity 38 of the burner 35 and has, in the case represented in FIG. 3, a transverse section smaller than the corresponding transverse section of the cavity 42 of the sleeve 36.

The burner 35 has a ring-shaped groove 44 substantially axial, extending from the upper surface 35c of the burner 35 and separating the peripheral zone 39 supporting the catalyst 10 from the central zone 41 without a catalyst creating a vaporisation zone.

This special structure of the upper part 35b of such a burner 35 was notably described in the patent EP 0 277 875 B1 in the applicant's name.

The burner 35 furthermore has a channel 45 to bring into contact with the atmosphere the upper part 38a of the cavity 38 purposed to hold the wick.

In the example represented in FIG. 3, the channel 45 is placed substantially axially. However, nothing prevents other placements for this channel 45, in particular the special placement represented in FIG. 8 of the document WO 99/63267.

Figure 4:
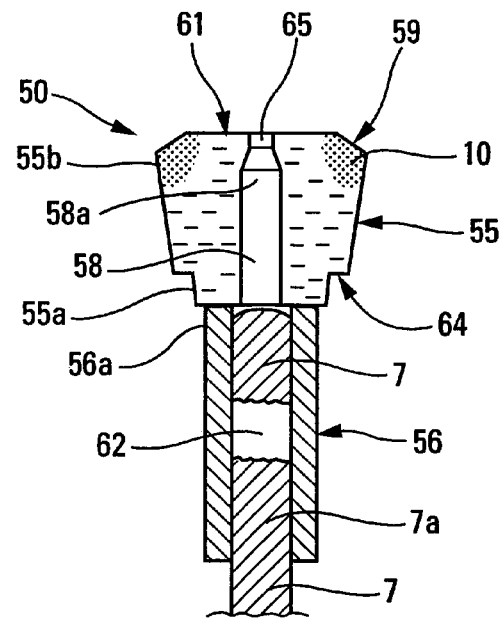
FIG. 4 is a similar view to that of FIG. 2 of a third embodiment of a burner system according to this invention.

A third alternative embodiment of a burner system according to the invention is represented in FIG. 4.

The burner system 50 represented in FIG. 4 comprises a catalytic combustion burner 55 and a sleeve 56.

This sleeve 56 is placed in line with the lower part 55a of the burner 55 and touches, at its upper part 56a, the lower part 55a of the burner 55.

This burner 55 has a tapered shape flared upwards.

The upper part 55b of the burner 55 comprises a peripheral zone 59 supporting a catalyst 10 and encircling a central zone 61 without a catalyst, as well as a cavity 58.

This cavity 58 is linked to the atmosphere at its upper part 58a, via the channel 65 located in the centre of the central zone 61.

The cavity 62 of the sleeve 56 can have a transverse section narrower than the corresponding transverse section of the cavity 58 of the burner 55.

The cavity 62 of the sleeve 58 is here completely taken up by the wick 7 which does not enter into the cavity 58 of the burner 55.

This special tapered shape of the burner allows the surface of vaporisation of the combustible composition to be increased and thus an improved diffusion of this composition in the ambient air of an enclosed space or part to be ensured.

The burner 55 can advantageously be fitted with at least one shoulder 64 purposed to restrict the part of the peripheral zone 59 which is purposed to hold the catalyst 10.

Incidentally, such a shoulder 64 works in conjunction with the sleeve 56 to allow for a matching positioning of the burner system 50 according to the invention on the flask 1 of FIG. 1, at its neck 4.

In the examples of embodiment which have just been described above but also generally speaking, the wick 7 is of any known type, for example a wick made from cotton.

It can of course be envisaged to use a wick made from mineral material, such as a wick made in mineral fibres.

The wick 7 is chosen so that its capillarity is largely superior to the radial and longitudinal capillarity of the sleeve 6.

The wick 7 is placed in the catalytic combustion flask so as to be immersed in the combustible composition 2 and is held, in the burner system 3, 30, 50, via its upper part 7a which is tightly held in the sleeve 6, 36, 56.

The sleeve 6, 36, 56 covers at least 10%, generally between 10% and 40%, advantageously between 20% and 30%, and preferably about 25% of the length of the wick 7.

The dimension of the sleeve 6, 36, 56 depends both on the porosity of the second porous material constituting the sleeve 6, 36, 56 and on the degree of clamping of the wick 7 in the said sleeve 6, 36, 56, in particular when the wick employed is made from cotton.

Usually, the wick 7 takes up the complete volume of the cavity 12, 42, 62 of the sleeve 6, 36, 56.

But it can also be planned that the said wick 7 in addition takes up all or part of the volume of the cavity 8, 38, 58 of the burner 5, 35, 55.

In the latter hypothesis, in particular when all the volume of the cavity 8, 38, 58 of the burner 5, 35, 55 is also taken up by the upper end of the wick 7, it is preferable to provide the burner 5, 35, 55 with a channel 45, 65 that brings the said cavity 8, 38, 58 into contact with the atmosphere so as to avoid any risk of carbonisation of the wick 7.

In any event, it is to be noted that, in the event of using a burner system 3, 30, 50, in which the upper part 7a of the wick 7 takes up the cavity 12, 42, 62 of the sleeve 6, 36, 56 but not the cavity 8, 38, 58 of the burner 5, 35, 55, no carbonisation of the wick 7 takes place, irrespective of whether a channel 45, 65 is present on the burner 5, 35, 55 or not.

It is also possible to plan for a burner system comprising a burner with a very simple structure.

Figure 5:
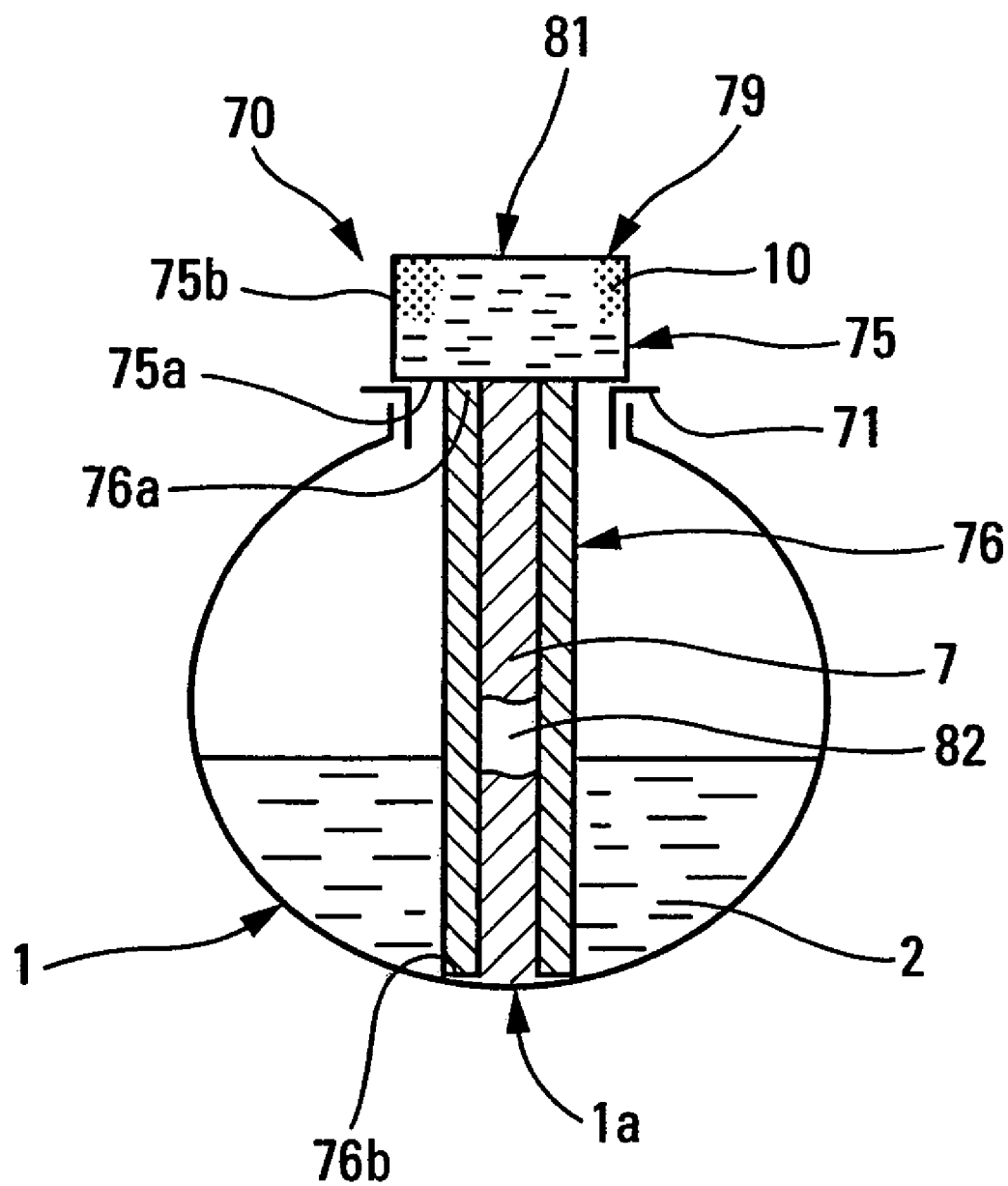
FIG. 5 is a similar view to that of FIG. 1 of a flask fitted with a catalytic combustion burner system according to a fourth embodiment, the said system being placed on a collar.

This is the case in the fourth alternative embodiment of a burner system according to the invention such as represented in FIG. 5.

The burner system 70 represented in FIG. 5 comprises a catalytic combustion burner 75 and a sleeve 76 joined via sealing at the lower part 75a of the burner 75 and at the upper part 76a of the sleeve 76.

The burner 75 comprises a peripheral zone 79 supporting a catalyst 10, this zone 79 encircling a central zone 81 without a catalyst.

On the other hand, and contrary to all the burner structures 5, 35 and 55 previously seen and represented in FIGS. 2 to 4, the burner 75 has a solid structure and does not have any cavity at its lower part 75a.

This burner 75 is placed on a support and/or collar 71 attached to the neck 4 of the flask 1.

In this particular embodiment of the burner system 70 represented in FIG. 5, the sleeve 76 takes up substantially the whole height of the flask 1. The lower part 76b of the sleeve 76 is close to the bottom 1a of the flask 1.

It is for example possible to envisage that the sleeve 76 has a telescopic structure so that its length can be adapted to the different heights of the flasks onto which the burner system 70 is planned to be used.

In addition, in this same FIG. 5, the entire cavity 82 of the sleeve 76 is taken up by the wick 7.

The burner 75 could also be used with the sleeve 76, without a wick.

Of course, this invention is not limited to the examples of embodiment that have just been described, and numerous changes and modifications can be added to these whilst keeping within the field of this invention.

Notably, the elements constituting the catalytic combustion burner system 3, 30, 50, 70, that being the catalytic combustion burner 5, 35, 55, 75 and the sleeve 6, 36, 56, 76, can be combined in whatsoever manner.

In particular, it can be planned to fit the upper part 5b, 55b and 75b of the burners 5, 55 and 75 respectively represented in FIGS. 2, 4 and 5, with a ring-shaped groove respectively separating the peripheral zones 9, 59, 79 from the central zones 11, 61, 81, such a groove having the characteristics of the ring-shaped groove 44 represented in FIG. 3.

It is also entirely possible to plan that the upper part of the cavity 8 of the burner 5 in FIG. 2 be linked to the atmosphere via a channel, such as those represented in FIGS. 3 and 4 and respectively comprising the references 45 and 65.

Additionally, the burner can be of any shape, and must not be understood to be limited to the represented cylindrical and tapered shapes.

Nothing prevents envisaging the embodiment of a catalytic combustion burner system according to the invention based on an already known burner available to date on the market, to which is added a sleeve 6, 36, 56, 76, under the reserve that the latter meets the aforementioned characteristics.

The invention claimed is:

1. Catalytic combustion burner system comprising a burner made from a first porous material and having on an upper part a peripheral zone supporting a catalyst and a central zone without a catalyst creating a vaporization zone, a sleeve made from a second porous material comprising a substantially axial cavity for holding tight a wick for carrying a combustible composition to the burner, said sleeve being placed in line with a lower part of the burner so that the combustible composition can move from pores of the upper part of the sleeve towards pores of the lower part of the burner, and said sleeve allowing controlling of the supply of combustible composition to the burner.

2. System according to claim 1, wherein the second porous material has a porosity preferably less than a porosity of the first porous material of the burner.

3. System according to claim 1, wherein the sleeve covers at least 10% of the length of the wick.

4. System according to claim 3, wherein the sleeve covers between 10% and 40% of the length of the wick.

5. System according to claim 3, wherein the sleeve covers between 20% and 30% of the length of the wick.

6. System according to claim 3, wherein the sleeve covers about 25% of the length of the wick.

7. System according to claim 1, wherein the burner and the sleeve are assembled via a porous sealing designed to ensure movement of the combustible composition from the sleeve towards the burner.

8. System according to claim 1, wherein the burner and the sleeve are one and the same part.

9. System according to claim 1, wherein the first and second porous materials are constituted from cordierite.

10. System according to claim 1, wherein the burner has a substantially axial ring-shaped groove extending from an upper surface of the burner and separating the peripheral zone supporting the catalyst from the central zone without a catalyst creating a vaporization zone.

11. System according to claim 1, wherein the burner has on its lower part a substantially axial cavity designed to hold the wick.

12. System according to claim 11, wherein the burner has a channel to bring an upper part of the substantially axial cavity of the burner into contact with the atmosphere.

13. System according to claim 11, wherein the wick is inserted in the substantially axial cavity of the sleeve and, if needed, into at least part of the substantially axial cavity of the burner.

14. Catalytic combustion flask, designed to contain a combustible composition and to be fitted with, on its neck, a catalytic combustion burner system designed to hold a wick immersed in the said combustible composition, wherein the flask is fitted with a burner system according to claim 1.

* * * * *